US010376335B2

(12) United States Patent
Azizian et al.

(10) Patent No.: US 10,376,335 B2
(45) Date of Patent: *Aug. 13, 2019

(54) METHOD AND APPARATUS TO PROVIDE UPDATED PATIENT IMAGES DURING ROBOTIC SURGERY

(71) Applicants: Siemens Healthcare GmbH, Erlangen (DE); Intuitive Surgical Operations, Inc., Sunnyvale, CA (US)

(72) Inventors: Mahdi Azizian, Santa Clara, CA (US); Lutz Blohm, Möhrendorf (DE); Holger Kunze, Bubenreuth (DE); Christine Niebler, Rückersdorf (DE); Jonathan Sorger, Belmont, CA (US)

(73) Assignees: Siemens Healthcare GmbH, Erlangen (DE); Intuitive Surgical Operatons, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,603

(22) PCT Filed: Sep. 10, 2015

(86) PCT No.: PCT/IB2015/056938
§ 371 (c)(1),
(2) Date: Nov. 20, 2017

(87) PCT Pub. No.: WO2016/185259
PCT Pub. Date: Nov. 24, 2016

(65) Prior Publication Data
US 2018/0153636 A1    Jun. 7, 2018

Related U.S. Application Data

(63) Continuation-in-part of application No. 14/716,963, filed on May 20, 2015, now Pat. No. 9,622,831.

(51) Int. Cl.
*A61B 90/00* (2016.01)
*A61B 34/30* (2016.01)
*A61B 34/00* (2016.01)

(52) U.S. Cl.
CPC .............. *A61B 90/37* (2016.02); *A61B 34/30* (2016.02); *A61B 34/25* (2016.02);
(Continued)

(58) Field of Classification Search
CPC ......... A61B 90/37; A61B 34/25; A61B 34/30; A61B 2090/364; A61B 2090/3762;
(Continued)

(56) References Cited

U.S. PATENT DOCUMENTS 7,155,316 B2   12/2006   Sutherland et al.
7,376,903 B2   5/2008    Morita et al.
(Continued)

FOREIGN PATENT DOCUMENTS

EP   2277441 A1   1/2011
JP   2011254975 A  12/2011
(Continued)

OTHER PUBLICATIONS

PCT International Search Report and Written Opinion of the International Searching Authority dated Feb. 29, 2016 for corresponding PCT/IB2015/056938.
(Continued)

Primary Examiner — Bo Joseph Peng
(74) Attorney, Agent, or Firm — Lempia Summerfield Katz LLC

(57) ABSTRACT

In a method and an apparatus to provide updated images during a robotically-implemented surgical procedure, 3D data is obtained of a volume of a patient, which includes anatomy involved in the procedure. The anatomy is segmented from a reconstructed image of the volume. During
(Continued)

the procedure, the surgeon applies forces on the anatomy, causing a geometric change of the anatomy. Force sensors in the surgical robot detect these forces, which are supplied to a processor that controls display of the segmented anatomy at a display screen. From the applied forces and the physical properties of the anatomy, the processor calculates the geometric change of the anatomy that has occurred and modifies the appearance and/or position of the displayed segmented anatomy on the display screen in real time during the procedure, so as to visualize the geometric change.

14 Claims, 2 Drawing Sheets

(52) U.S. Cl.
CPC ... *A61B 2090/064* (2016.02); *A61B 2090/364* (2016.02); *A61B 2090/367* (2016.02); *A61B 2090/368* (2016.02); *A61B 2090/3762* (2016.02)

(58) Field of Classification Search
CPC ........ A61B 2090/367; A61B 2090/368; A61B 2090/064
See application file for complete search history.

(56) References Cited

U.S. PATENT DOCUMENTS

| | | | | |
|---|---|---|---|---|
| 2001/0025183 A1* | 9/2001 | Shahidi | ................. | A61B 90/10 606/130 |
| 2003/0216836 A1* | 11/2003 | Treat | ..................... | A61B 90/96 700/245 |
| 2004/0128026 A1* | 7/2004 | Harris | .................... | B25J 9/1689 700/245 |
| 2006/0142657 A1* | 6/2006 | Quaid | ..................... | G06F 19/00 600/424 |
| 2010/0168918 A1 | 7/2010 | Zhao | | |
| 2010/0274087 A1* | 10/2010 | Diolaiti | .................. | A61B 90/37 600/118 |
| 2011/0077504 A1* | 3/2011 | Fischer | .................. | A61B 34/30 600/411 |
| 2011/0201885 A1* | 8/2011 | Okamura | ............... | B25J 9/1671 600/109 |
| 2011/0306985 A1 | 12/2011 | Inoue et al. | | |
| 2012/0265051 A1* | 10/2012 | Fischer | .............. | A61B 10/0241 600/411 |
| 2013/0345718 A1* | 12/2013 | Crawford | ............. | A61B 17/025 606/130 |
| 2014/0051922 A1 | 2/2014 | Guthart et al. | | |
| 2014/0094968 A1 | 4/2014 | Taylor et al. | | |
| 2016/0070436 A1 | 3/2016 | Thomas et al. | | |

FOREIGN PATENT DOCUMENTS

| | | |
|---|---|---|
| JP | 2012235983 A | 12/2012 |
| WO | 2014139024 A1 | 9/2014 |

OTHER PUBLICATIONS

European Search Report for European Patent Application No. 15892502A-1126 / 3282994 dated Nov. 14, 2018.
Japanese Office Action for Japanese Patent Application No. 2017-559816, dated Jan. 29, 2019, with English Translation.

* cited by examiner

METHOD AND APPARATUS TO PROVIDE UPDATED PATIENT IMAGES DURING ROBOTIC SURGERY

The present patent document is a § 371 nationalization of PCT Application Serial Number PCT/IB2015/056938, filed Sep. 10, 2015, designating the United States, which is hereby incorporated by reference, and this patent document also claims the benefit of U.S. patent application Ser. No. 14/716,963, filed May 20, 2015, which is also hereby incorporated by reference.

TECHNICAL FIELD

The present disclosure concerns imaging systems and procedures used to provide images during the course of a surgical procedure implemented by a robotic manipulator.

BACKGROUND

Robotically implemented medical procedures, commonly called robotic surgery, is in widespread use for a variety of medical interventional procedures involving many different organs of a patient. Particularly in the case of abdominal procedures, such as those involving the pancreas or the liver, the organ in question is physically moved or otherwise modified by the robotic manipulator during the course of the procedure. Such changes are designated below as geometric changes to the region or anatomy. Similar changes in the organ or the region of interest also occur at other sites within the patient.

As is well known, commercially available robotic manipulators are operated by a physician (surgeon) to execute a number of physical interactions with one or more organs during the procedure, such as grabbing, cutting, pushing, pulling, etc. It may be the case that the surgical site is resected in order to expose the organ that is being manipulated, but certain types of procedures may also be implemented with only a small incision for introducing an instrument or endoscope.

A computed tomography or magnetic resonance image of the surgical site may be obtained as part of a planning procedure. During the actual procedure, an endoscopic image may be obtained, and the content of such an endoscopic image is thus limited by the field of view of the camera that is used to obtain the endoscopic image. The endoscopic image may include only contents that are within the direct line of sight of the camera and thus only the sides of organs and surrounding tissue that are facing the camera may be seen in such an image.

Although the organ of interest in the planning image may be segmented and then rotated, translated, or otherwise changed in known ways at the display screen, the planning image, since it was obtained before the surgical procedure started, will not show changes in the organ itself, such as cutting thereof, that occur during the course of the surgical procedure, and also will not show changes in the position of the organ that may also occur during the course of the procedure.

Known robotic manipulators that are used in surgical procedures are operated from a control console, at which the surgeon is situated. The control console includes a number of manually operated or manipulated elements that the physician operates in the same manner as if the physician were using an instrument at the actual site of the surgery. Thus, for example, if the physician wants to implement a cutting procedure on the organ via the robotic manipulator, a scissors-like control element will be provided at the console. The corresponding cutter of the robotic manipulator is provided with appropriate force sensors, which detect forces at the organ that are applied by the robotic manipulator, and also detect forces on the robotic manipulator that are produced by the organ. This combination of forces provides haptic feedback to the surgeon at the console so that the surgeon operating the scissors-like control element will experience the same cutting force, and resistance of the organ to such a cutting force, that the surgeon would feel if the physician were directly manually operating a cutting element at the surgery site.

The same is true with regard to other types of instruments that are implemented by the robotic manipulator, such as instruments that grab the organ in order to allow the surgeon to then displace all or a portion of the organ in a selected manner.

SUMMARY

An object of the present disclosure is to provide a surgeon with one or more displayed images during the course of a robotically-implemented surgical procedure that not only show the current state of the anatomy or organ that is the subject of the intervention, but also allow the surgeon, by manipulating the displayed images, to see portions of the anatomy that are not visible in a conventional endoscopic image.

The scope of the present disclosure is defined solely by the appended claims and is not affected to any degree by the statements within this summary. The present embodiments may obviate one or more of the drawbacks or limitations in the related art.

This object is achieved by a method and an apparatus wherein 3D data are obtained of a volume of a patient, which includes anatomy such as a selected organ, which is to be the subject of a robotically-implemented surgical procedure. The anatomy or organ of interest is then segmented from an image of the aforementioned volume that has been reconstructed from the 3D data. The segmentation may be done either manually or by a computerized pattern recognition segmentation algorithm. During the course of the robotically implemented surgical intervention, the surgeon causes one or more forces on the anatomy or organ to occur that cause a modification or displacement of the anatomy or organ (e.g., geometric change). These forces are known by being detected by the force sensors that are conventionally present in commercially available robotic manipulators. These forces are supplied to a processor that controls the display of the segmented anatomy or organ at a display screen that is viewed by the surgeon or an assistant during the procedure. The processor calculates the amount of modification or displacement of the anatomy or organ that has occurred as a result of the applied forces and as a result of the physical properties of the anatomy or organ. The processor then automatically modifies the appearance and/or position of the displayed segmented anatomy or organ on the display screen in real time during the procedure, so that the surgeon has a current visualization of the state of the anatomy or organ as the procedure progresses. Additionally, because the organ or anatomy has been segmented, all conventional operations that may be applied to displayed, segmented anatomy may be implemented by the surgeon during the procedure, such as rotation, translation, etc. For example, if an anterior view of the anatomy or organ is being displayed, the physician may rotate the organ to obtain a posterior view, which would normally not be able to be seen in the conventional endoscopic images that are used during such procedures.

The data representing the physical properties of the anatomy or organ that is the subject of the surgical intervention, which are used in combination with the forces applied by the robotic manipulator in order to computationally determine the resulting modification or displacement of the anatomy or organ, may be obtained from an anatomical atlas. Such an atlas may be compiled for respective anatomy or organs of a general patient population, or may be more specifically matched to a patient population comparable to the patient who is undergoing the procedure. For example, an atlas may be compiled for patients of an age or medical history comparable to that of the patient, patients exhibiting the same pathological condition of the relevant anatomy or organ, etc.

The present disclosure also encompasses a non-transitory, computer-readable data storage medium that is encoded with programming instructions that, when executed by one or more processors in which the storage medium is loaded, or that have access to the loaded storage medium, cause any or all of the above embodiments of the method to be implemented. The storage medium may be loaded into a processor of a central workstation that controls the overall functions performed during the course of a robotically-implemented surface procedure, or the programming instructions may be distributed appropriately among respective processors that individually have responsibility for controlling a subset of the complete suite of functions.

DETAILED DESCRIPTION

Figure 1:
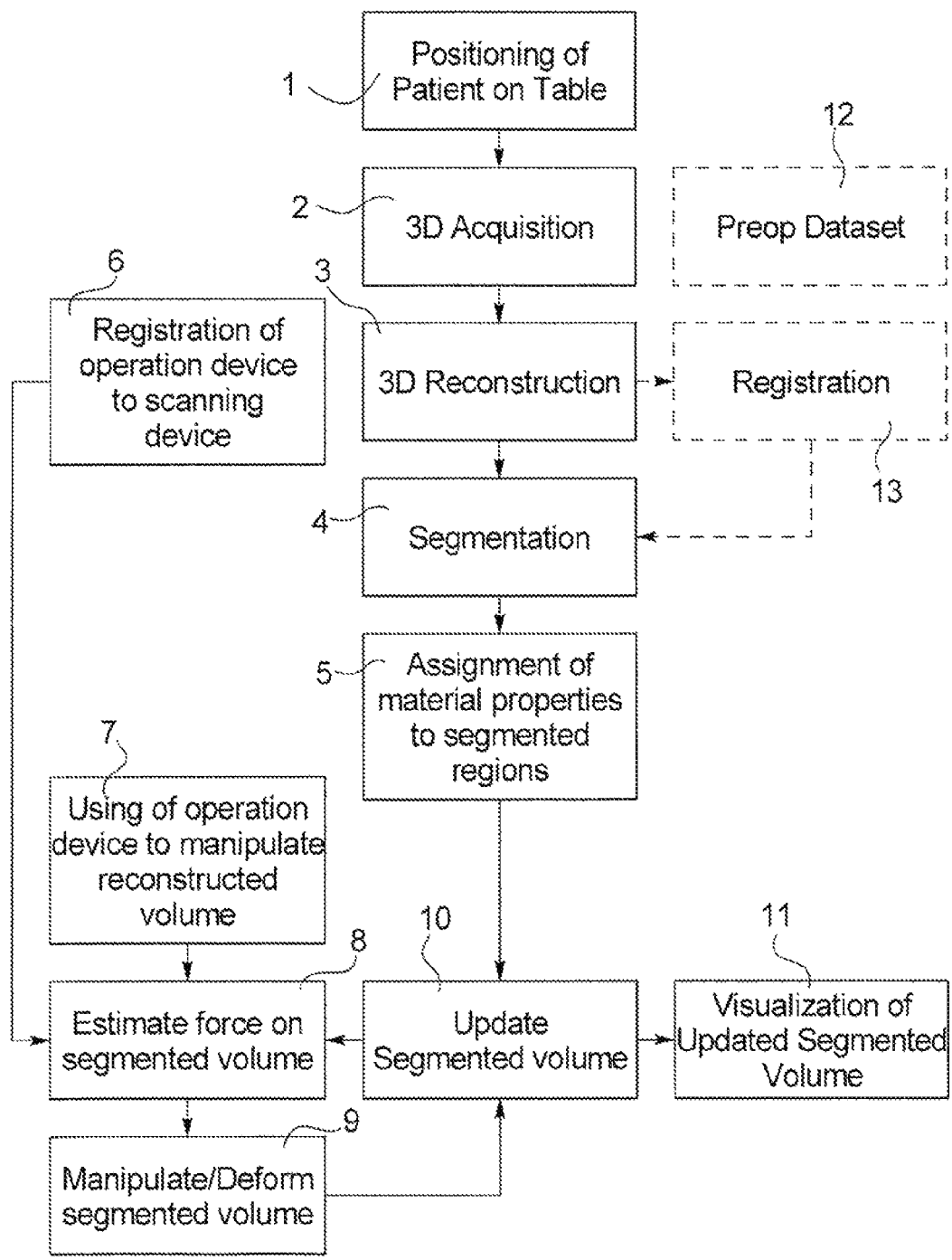
FIG. 1 is a flowchart showing various acts of the method in accordance with an example, with optional acts being shown in dashed lines.

As shown in the flowchart of FIG. 1, the method begins in act 1 with the positioning of a patient on a table in a surgical venue. The patient is to undergo a robotically-implemented surgical procedure in the operating venue, while on the table.

After the patient has been placed on the table, 3D data is acquired in act 2 from a volume of the patient that includes the anatomy or the organ that is to be the subject of the robotically-manipulated surgical intervention.

In act 3, the acquired 3D data is supplied to a processor, which implements a 3D reconstruction algorithm to generate a 3D image of the volume of the patient represented by the acquired 3D data.

In act 4, the specific anatomy or organ that is the subject of the intervention is segmented from the overall 3D image of the volume. This may be implemented manually, such as by interaction of the surgeon with the displayed image on a screen, with the surgeon using a light pen or cursor to outline the organ or anatomy to be segmented. The segmentation alternatively may be implemented completely automatically, using known pattern recognition-based segmentation algorithms.

An option is to provide, in act 12, a pre-operative data set of the patient, which may be a data set representing one or more medical images of the patient that have been acquired in previous examinations of the patient. Such a pre-operative 3D data set may include any of the known techniques that are used to highlight or enhance selected anatomy or pathological conditions, such as by color coding, contrast agent enhancement, fMRI images in the case of brain surgery being implemented, diffusion-weighted images, etc.

If such a pre-operative data set is optionally provided in act 12, this pre-operative data set is then brought into registration with the aforementioned 3D reconstructed image of the patient on the table in act 13, and the segmentation may then be implemented in order to segment the anatomy or organ from the registered, pre-operative data set combined with the reconstructed volume image.

Following the segmentation, material properties are assigned by the processor to the segmented regions in act 5. These material properties are known or expected properties of the segmented anatomy that are provided to the processor, such as by the processor having access to an anatomical atlas. The anatomical atlas may provide a listing of relevant material properties of many different anatomical regions or organs, and the processor then selects the appropriate set of properties from the atlas that correspond to the segmented region. As noted above, the atlas may be compiled for a general patient population, or may be more specifically directed to patients comparable to the patient on whom the surgical procedure is to be implemented. For example, the atlas may be compiled from patients of the same age group as the patient, patients exhibiting the same pathological conditions of the segmented anatomy as the patient, patients having a medical history similar to that of the patient, etc.

In parallel with, or interleaved with, the aforementioned acts, in act 6 the coordinate system of the operation device (e.g., robotic manipulator) that is to be used in the procedure is brought into registration with the coordinate system of the scanning device, with which the aforementioned 3D image of the patient on the table was acquired. This registration of these coordinate systems may be implemented in any known manner, such as by knowledge of the physical relationship of the coordinate systems that results by virtue of the physical mounting of the operation device on the patient table, or by markers attached at suitable locations on the operation device that are visible in the acquired 3D data of the patient on the patient table, in which case the operation device is also within the field of view of the scanning device. Suitable navigation systems are also known that identify the respective coordinate systems of the operation device and the scanner, and bring those coordinate systems into registration with each other.

The interventional procedure is then started, using the operation device in order to selectively manipulate anatomy or an organ within the reconstructed volume (act 7). Commercially available operation devices, such as robotic manipulators, provide haptic feedback to the surgeon who is operating the device, and for this purpose contain force sensors that detect forces that are applied to the anatomy or organ by the operation device during the course of the procedure. The processor that is used by the operation device to provide the haptic feedback thus may already provide an accurate estimate of the force or forces that are applied to the anatomy or organ during the procedure, and the output of this processor may be provided to the processor that controls display of the segmented region at a display screen situated at the operation venue, which may be seen by the surgeon during the course of the procedure.

Alternatively, the outputs of these force sensors may be directly supplied to the processor, and the processor may generate its own estimate of the force or forces that have been applied to the segmented volume.

Either type of estimation takes place in act 8.

Based on the estimated force or forces applied to the segmented volume at any given time during the procedure, and based on the material properties of the segmented regions, the processor automatically determines in act 9, modification or displacement of the organ or anatomy that has occurred, and updates the display of the segmented volume in act 10 in order to incorporate such modification or displacement. This updated segmented volume is then visualized at the display in act 11, and may be selectively manipulated by the surgeon of a segmented volume, such as by rotation or translation thereof.

The surgeon thus not only sees the state of the segmented anatomy or organ as it changes during the course of the procedure, but also may manipulate the updated (e.g., current) segmented volume so as to obtain views thereof that would not be available from a conventional endoscopic image, which may only detect the side of the anatomy or organ that is facing the endoscopic camera.

Figure 2:
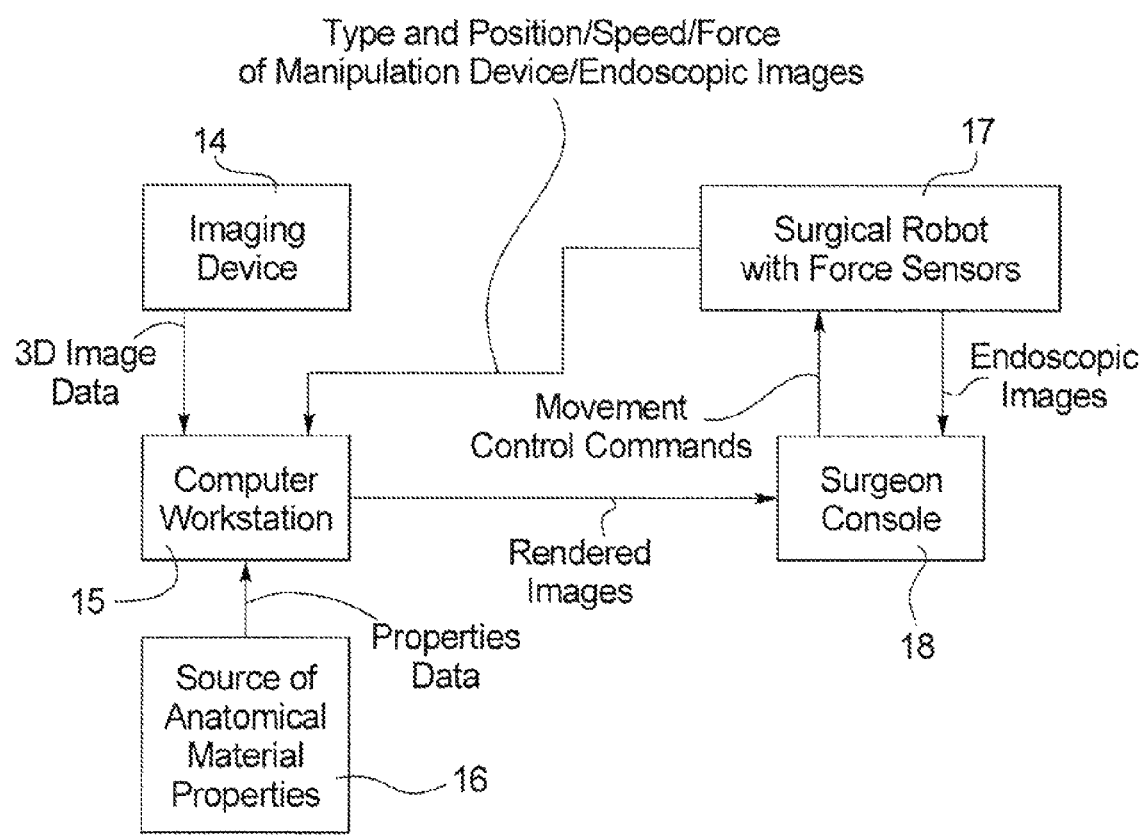
FIG. 2 is a block diagram showing the various components of an apparatus constructed and operating in accordance with an example the present disclosure.

FIG. 2 is a block diagram illustrating the basic components of the apparatus. The apparatus includes an imaging device or system 14, such as a C-arm x-ray imaging system mounted on a robot. Such a system may be, for example, the Artis VD 11 angio-system that is commercially available from Siemens Healthcare. The system may include suitable collision monitoring components and other control modules of the type that are conventionally available for use in a surgical environment. The imaging system 14 includes a patient table, on which the patient lies during the procedure, to which a surgical robot 17 is mounted. The surgical robot is operated from a surgeon console 18, which includes any number of control elements that are manipulated by the surgeon during the course of the procedure. The manipulations that are made by the surgeon at the console are translated to movements of the surgical robot, including the operation of tools or instruments carried by the surgical robot, such as scissors, grabbers, etc. The surgeon console provides appropriate control commands to the robot that cause the aforementioned actions to be implemented. The robot may carry an endoscopic camera having a field of view that encompasses the surgery site, so that endoscopic images of the surgery site are provided to the surgeon at the surgeon console.

The imaging system is operated by a computer at a workstation (e.g., control console) 15 to acquire the aforementioned 3D images of the patient on the table, such as CT images. The acquired 3D data are reconstructed to show an image of the acquired region, from which anatomy or an organ of interest is then segmented at the workstation 15. The aforementioned endoscopic images may also be supplied to the workstation 15, as are the forces detected by the force sensors that are present at the surgical robot 17. From this applied force information, and the aforementioned material properties of the segmented regions that are known to the processor at the workstation 15 from a source 16, the updating of the segmented regions, as described above, takes place at the workstation 15, so that the updated segmented images incorporate changes and displacements to the segmented anatomy or organ that have occurred during the course of the intervention. The updated segmented region may be displayed at a display screen of the workstation 15, which is visible by the surgeon from the surgeon console, or may be supplied to the display screen at the surgeon console 18 for display together with the endoscopic images. The updated segmented regions may be manipulated by the surgeon either via controls that are made available directly at the surgeon console, or that are available at the workstation. The surgeon may simultaneously be able to operate the workstation 15, or may provide oral directions to an assistant situated at the workstation 15 in order to manipulate the updated segmented image as the surgeon directs.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

We claim as our invention:

1. A method for providing current images of a surgical site during a surgical procedure, the method comprising:
   receiving, by an imaging system, three-dimensional (3D) data representing a volume of a patient on a patient table from a medical imaging device of the imaging system, the volume comprising an anatomy to be manipulated, during a surgical procedure, by a surgical robot;
   constructing, by the imaging system, a 3D image of the volume from the 3D data;
   constructing, by the imaging system, a segmented 3D volumetric image of the anatomy from the 3D image of the volume;
   bringing, by the imaging system, a coordinate system of the surgical robot into registration with a coordinate system of the medical imaging device;
   receiving, by the imaging system, a signal representing at least one force applied to the anatomy during the surgical procedure and detected by a force sensor of the surgical robot, wherein the at least one force produces a geometrical change of the anatomy;
   automatically updating, by the imaging system, the segmented 3D volumetric image of the anatomy, based on the at least one force, to produce an updated segmented 3D volumetric image of the anatomy that visually shows the geometrical change of the anatomy; and
   displaying, by a display screen of the imaging system, the updated segmented 3D volumetric image of the anatomy in real-time during the surgical procedure.

2. A method as claimed in claim 1, further comprising:
   storing at least one material property respectively for different anatomical objects in an electronic database, wherein the at least one material property is a same or different material property for each anatomical object, and
   accessing the electronic database from the processor to obtain the at least one material property from the database for the anatomy in the segmented 3D volumetric image.

3. A method as claimed in claim 2, further comprising:
obtaining a pre-operative data set of the patient prior to receiving the 3D data of the patient on the table, the pre-operative data comprising the volume of the patient that is comprised in the 3D data;
providing the pre-operative data set to the processor;
bringing, by the processor, the pre-operative data set into registration with the 3D image constructed from the 3D data and then combining the pre-operative data set with the 3D image constructed from the 3D data to generate a combined image; and
segmenting the anatomy from the combined image to obtain the segmented 3D volumetric image of the anatomy.

4. A method as claimed in claim 1, further comprising:
obtaining an endoscopic image of the anatomy and displaying the endoscopic image of the anatomy at the display screen or a second display screen during the surgical procedure; and
during the surgical procedure, manipulating the updated segmented 3D volumetric image of the anatomy to show a view of the anatomy that is not visible in the endoscopic image.

5. A method as claimed in claim 1, further comprising:
segmenting the anatomy from the 3D image of the volume constructed from the 3D data by interaction, via the processor, with the 3D image of the volume constructed from the 3D data.

6. A method as claimed in claim 1, further comprising:
automatically segmenting the anatomy, by the processor, from the 3D image of the volume constructed from the 3D data, by executing a segmentation algorithm with pattern recognition.

7. An apparatus for providing current images of a surgical site during a surgical procedure, the apparatus comprising:
a control computer having at least one processor, the control computer configured to operate a medical imaging device to acquire three-dimensional (3D) data representing a volume of a patient on a patient table, the volume comprising anatomy to be manipulated during a surgical procedure by a surgical robot; and
a display screen in communication with the at least one processor of the control computer,
wherein the at least one processor of the control computer is configured to construct a 3D image of the volume from the 3D data,
wherein the at least one processor is configured to construct a segmented 3D volumetric image of the anatomy from the 3D image of the volume,
wherein the at least one processor is configured to bring a coordinate system of the surgical robot into registration with a coordinate system of the medical imaging device,
wherein the at least one processor is configured to receive an electronic signal representing at least one force applied to the anatomy during the surgical procedure and detected by a force sensor of the surgical robot, wherein the at least one force produces a geometrical change of the anatomy,
wherein the at least one processor is configured to automatically update the segmented 3D volumetric image of the anatomy, based on the at least one force, to produce an updated segmented 3D volumetric image of the anatomy that visually shows the geometrical change of the anatomy, and
wherein the at least one processor is configured to display the updated segmented 3D volumetric image of the anatomy in real-time during the surgical procedure at the display screen.

8. An apparatus as claimed in claim 7, further comprising:
an electronic database in which at least one material property respectively for different anatomical objects is stored, wherein the at least one material property is a same or different material property for each anatomical object, and
wherein the processor is configured to access the electronic database to obtain the at least one material property from the database for the anatomy in the segmented 3D volumetric image.

9. An apparatus as claimed in claim 8, further comprising:
a source of a pre-operative data set acquired from the patient prior to receiving the 3D data of the patient on the table, the preoperative data comprising the volume of the patient that is comprised in the 3D data;
wherein the processor is configured to receive the pre-operative data set and to bring the pre-operative data set into registration with the 3D image constructed from the 3D data, and then combine the pre-operative data set with the 3D image constructed from the 3D data, and
wherein the processor is configured to segment the anatomy from the combined image to obtain the segmented 3volumetric image of the anatomy.

10. An apparatus as claimed in claim 7, further comprising:
an endoscopic camera at the surgical robot, wherein the endoscopic camera is configured to obtain an endoscopic image of the anatomy and display the endoscopic image of the anatomy at the display screen or a second display screen during the surgical procedure,
wherein the control computer is configured to allow, during the surgical procedure, a manipulation of the updated segmented 3D volumetric image of the anatomy to show a view of the anatomy that is not visible in the endoscopic image.

11. An apparatus as claimed in claim 7, further comprising:
a user interface configured to allow segmenting of the anatomy from the 3D image of the volume constructed from the 3D data by interaction with the at least one processor, via the interface, with the 3D image of the volume constructed from the 3D data.

12. An apparatus as claimed in claim 7, wherein the at least one processor is configured to automatically segment the anatomy from the 3D image of the volume constructed from the 3D data, by executing a segmentation algorithm with pattern recognition.

13. A non-transitory, computer-readable data storage medium encoded with programming instructions, the storage medium being loaded into a computer of a surgery facility comprising a patient table configured to receive a patient thereon, a medical imaging device, and a surgical robot comprising an instrument that is operable during a surgical procedure, and a force sensor that detects a force applied by the instrument to anatomy of the patient that is involved in the surgical procedure, the programming instructions causing the computer to:
receive three-dimensional (3D) data representing a volume of a patient on the patient table, the volume comprising an anatomy to be manipulated, during a surgical procedure, by a surgical robot;

construct a 3D image of the volume from the 3D data;
construct a segmented 3D volumetric image of the anatomy from the 3D image of the volume;
bring a coordinate system of the surgical robot into registration with a coordinate system of the medical imaging device;
generate an electronic signal representing at least one force applied to the anatomy during the surgical procedure and detected by a force sensor of the surgical robot, wherein the at least one force produces a geometrical change of the anatomy;
automatically update the segmented 3D volumetric image of the anatomy, based on the at least one force, to produce an updated segmented 3D volumetric image of the anatomy that visually shows the geometrical change of the anatomy; and
display, at a display screen, the updated segmented 3D volumetric image of the anatomy in real-time during the surgical procedure.

14. A medical device system comprising:
a medical imaging system;
a surgical robot;
a display showing an updated segmented three-dimensional (3D) volumetric image of anatomy of a patient, the updated segmented 3D image of the anatomy showing in real time a geometrical change of the anatomy caused by the surgical robot during a surgical procedure; and
a processor that executes coded instructions to:
bring a coordinate system of the medical imaging device and a coordinate system of the surgical robot into registration;
receive 3D data from the medical imaging device during the surgical procedure, the 3D data representing a volume of the patient comprising the anatomy;
generate a 3D image of the volume from the 3D data;
generate a first segmented 3D volumetric image of the anatomy from the 3D image of the volume;
receive a signal representing a force on the anatomy by the surgical robot causing the geometrical change of the anatomy; and
generate the updated segmented 3D volumetric image of the anatomy from the first segmented 3D volumetric image of the anatomy by using the registration and the signal representing the force on the anatomy.

* * * * *